United States Patent
La Vean et al.

[11] Patent Number: 5,857,959
[45] Date of Patent: Jan. 12, 1999

[54] CONCEPTION KIT

[75] Inventors: Michael La Vean; Janet Tlapek, both of Saranac, Mich.

[73] Assignee: Veos France EURL, Saint Aubin Cedex, France

[21] Appl. No.: 794,562

[22] Filed: Feb. 3, 1997

[51] Int. Cl.$^6$ .................................................. A61B 17/43
[52] U.S. Cl. .......................................................... 600/33
[58] Field of Search ................ 600/33–35; 128/830–841

[56] References Cited

U.S. PATENT DOCUMENTS

| | | |
|---|---|---|
| 2,079,022 | 5/1937 | Martin . |
| 2,141,040 | 12/1938 | Holt . |
| 2,324,656 | 7/1943 | Vincent . |
| 2,423,356 | 7/1947 | Waterbury . |
| 2,818,856 | 1/1958 | Kohl . |
| 2,836,177 | 5/1958 | Sells . |
| 3,371,664 | 3/1968 | Pleshette . |
| 3,952,737 | 4/1976 | Lipfert et al. . |
| 4,198,965 | 4/1980 | Strickman et al. . |
| 4,198,976 | 4/1980 | Drobish et al. . |
| 4,200,090 | 4/1980 | Drobish . |
| 4,200,091 | 4/1980 | Del Conte . |
| 4,219,016 | 8/1980 | Drobish et al. . |
| 4,300,544 | 11/1981 | Rudel . |
| 4,304,226 | 12/1981 | Drobish et al. . |
| 4,311,543 | 1/1982 | Strickman et al. . |
| 4,320,751 | 3/1982 | Leeb . |
| 4,360,013 | 11/1982 | Barrows . |
| 4,381,771 | 5/1983 | Gabbay . |
| 4,393,871 | 7/1983 | Vorhauer et al. . |
| 4,401,534 | 8/1983 | Goepp et al. . |
| 4,553,972 | 11/1985 | Vickery . |
| 4,589,880 | 5/1986 | Dunn et al. . |
| 4,630,602 | 12/1986 | Stickman et al. . |
| 4,703,752 | 11/1987 | Gabbay . |
| 4,770,167 | 9/1988 | Kaali et al. . |
| 4,785,804 | 11/1988 | Tlapek et al. . |
| 4,895,170 | 1/1990 | Tlapek et al. . |
| 4,959,216 | 9/1990 | Daunter . |
| 5,027,830 | 7/1991 | Koch . |
| 5,044,376 | 9/1991 | Shields . |
| 5,070,889 | 12/1991 | Leveen et al. . |

FOREIGN PATENT DOCUMENTS

5471/31  12/1931  Australia .

*Primary Examiner*—John P. Lacyk
*Attorney, Agent, or Firm*—Harness, Dickey & Pierce, P.L.C.

[57] ABSTRACT

A conception cap comprising a thin, form-assuming, flexible dome, an annular rim, and thin, gripping fingers along the inner surface of the rim that make up a notched indentation to effectively position and secure the cap over the cervix for the concentration of sperm on the cervical Os to effect fertilization independently or with the aid of biologically active agents. The conception cap is also included as a component in a conception kit, allowing a woman to conduct the steps of the method of conception using the kit in the privacy of her home.

18 Claims, 2 Drawing Sheets

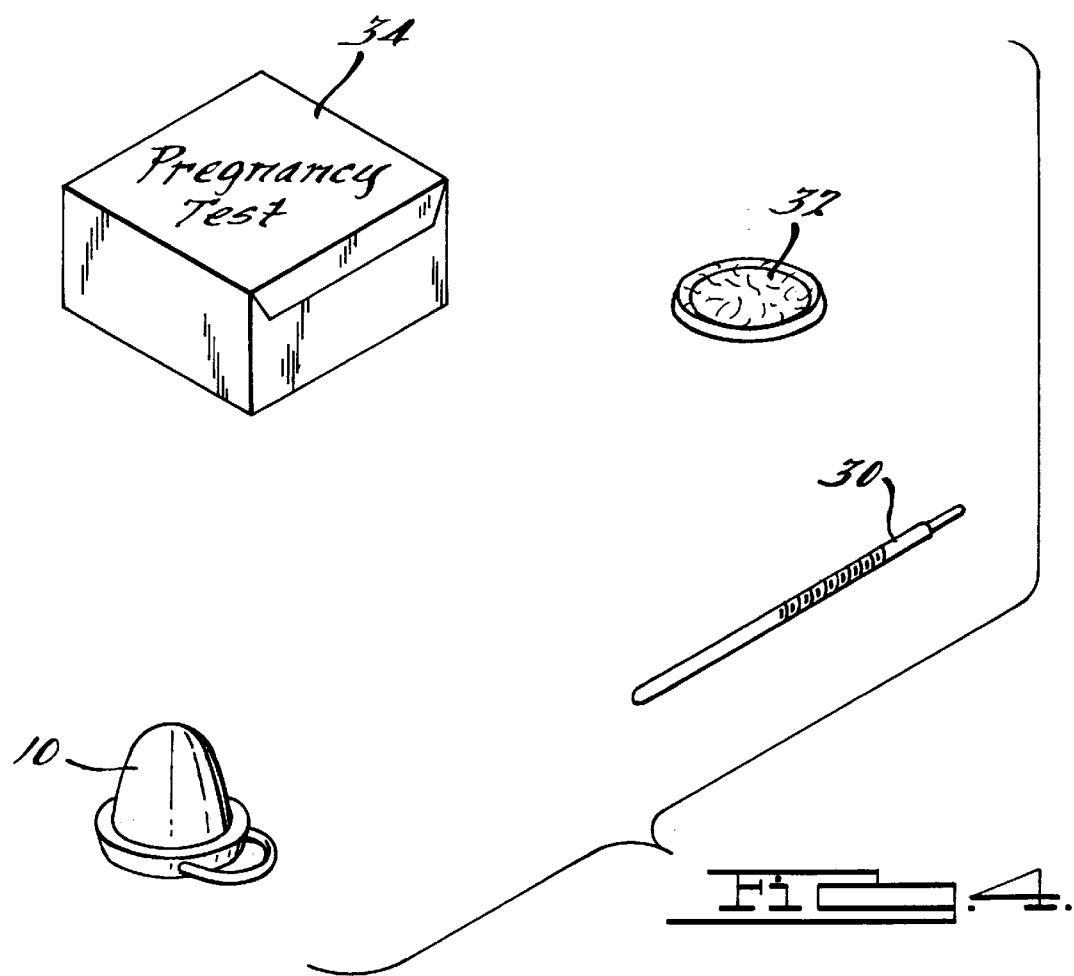

CONCEPTION KIT

BACKGROUND OF THE INVENTION

1. Field of the Invention

The present invention relates generally to a conception kit used to concentrate sperm and effect fertilization, and to a method of conception utilizing the kit. More particularly, the present invention encompasses a conception cap used to deliver increased concentrations of sperm to the cervical Os.

2. Discussion of the Related Art

Devices which are intended to be inserted into the vagina are known for use as contraceptive barriers. One particular contraceptive device, the cervical cap, is placed over the cervix to prevent semen from entering the cervical canal and is held in place by a suction grip or surface viscosity on the moist cervical surface. Some of these previous cervical caps are made of latex. However, since latex causes sperm damage, possibly resulting in deformed or abnormal children, the latex cap cannot be used for delivery of sperm. In addition, all of these devices are geared only towards the prevention of pregnancy.

Currently, however, there are parts of the population that are experiencing a decline in fertility and would benefit from an invention that increases the likelihood of conception. Some of the primary factors contributing to a decline in fertility are low sperm counts, problems with sperm motility, and a hostile vaginal environment due to infection or other chronic conditions. A method used to overcome these problems is sperm concentration at the cervical Os, which is the area connecting the uterus and the vaginal cavity. Sperm concentration significantly increases the probability of conception, as fewer sperm are needed to effect fertilization since a higher number reach the uterus intact. Since these sperm travel a shorter distance, a higher proportion remain viable upon reaching the uterus. In cases of low sperm counts or poor motility, this is particularly effective. In addition, a potentially hostile vaginal environment is bypassed.

Methods in use today to address fertility issues are administered only by medical professionals and are very costly. As an example, administration of sperm using a pipet that is inserted through the Os damages fragile cervical tissue and can cause extensive bleeding. In addition, the medical procedure is painful and involves considerable investments of time and money.

Modern technology allows for a woman to reliably predict ovulation, and assess her ability to become pregnant. In addition, sperm can be easily collected in a condom and thereby be mechanically confined to a small volume. Pregnancy tests are available and allow the woman to monitor her success. There is a need, therefore, for an inexpensive vaginal device that can be inserted by a woman and remain in place for an extended period of time. There is also a need for a kit that would provide a woman with all of the materials needed to successfully carry out a sperm concentration procedure at the appropriate biological time and monitor her success.

The present invention provides an improved method and conception cap for concentrating sperm and successfully effecting fertilization, overcoming the aforementioned problems. The conception cap of the present invention is made of a silicone-based material and can be positioned and secured over the cervix while containing sperm to facilitate conception. Moreover, all of the materials to allow a woman to effect this multi-day procedure and monitor its efficacy at a biologically appropriate time in an inexpensive and expedient manner are provided in a conception kit.

SUMMARY OF THE INVENTION

The present invention relates to a conception cap which is positioned over a female's cervix to increase the chances of successful fertilization. The dome of the conception cap has a hollow body and an interior and exterior surface. Further, the dome is designed to contain sperm, and upon insertion, provide a higher concentration of said sperm to the cervical Os. The dome is also thin, flexible, and form-assuming, allowing the conception cap to remain in place over the cervix until removed.

The conception cap of the present invention is additionally held in place over the cervix by an annular rim that is integrally-molded with the base section of the dome. The inner surface of the rim comprises at least two thin, gripping fingers that are utilized to keep the cap positioned over the cervix. The fingers are directly opposite or symmetrically opposed from each other along the inner surface of the rim and define a notched indentation which helps grip the cervix walls. Thus, the thinness of the dome and the rim construction eliminate the need for individual fittings for a large percentage of the female population, increase sperm concentration at the opening of the cervix, and minimize the possibility of dislodging the cap from its position over the cervix.

A handle or loop integrally-molded to the outer surface of the rim aids insertion and removal of the device. While the conception cap is in use, the handle is compressed between the cervix and the vaginal walls.

The present invention is also directed to a conception cap that comprises biologically active material which would assist in fertilization, or to which the biologically active material can be mixed with sperm within the hollow body of the dome of the cap in order to achieve the desired result.

The use of biologically active materials in either embodiment may stimulate sperm motility, prolong the active life of the sperm or aid in gender selection. Selectively eliminating or altering the behavior of some sperm by significantly changing the pH may bias the activity of the X or Y sperm, resulting in odds which favor one particular sex over the other.

The present invention is also directed to a conception kit used to concentrate sperm and effect fertilization. The kit comprises an ovulation predictor, a conception cap, a condom, and a pregnancy test. The conception kit provides the woman with the means to effect sperm concentration at a biologically appropriate time, aid fertilization and determine the success of her efforts.

The present invention further comprises a method of achieving conception utilizing the components of the conception kit, including the conception cap, to increase the chances of successful fertilization.

Additional advantages and features of the present invention will become apparent from the subsequent description and the appended claims, taken in conjunction with the accompanying drawings.

BRIEF DESCRIPTION OF THE DRAWINGS

FIG. 4 is a perspective view of a conception kit.

DETAILED DESCRIPTION OF THE PREFERRED EMBODIMENT

Figure 1:
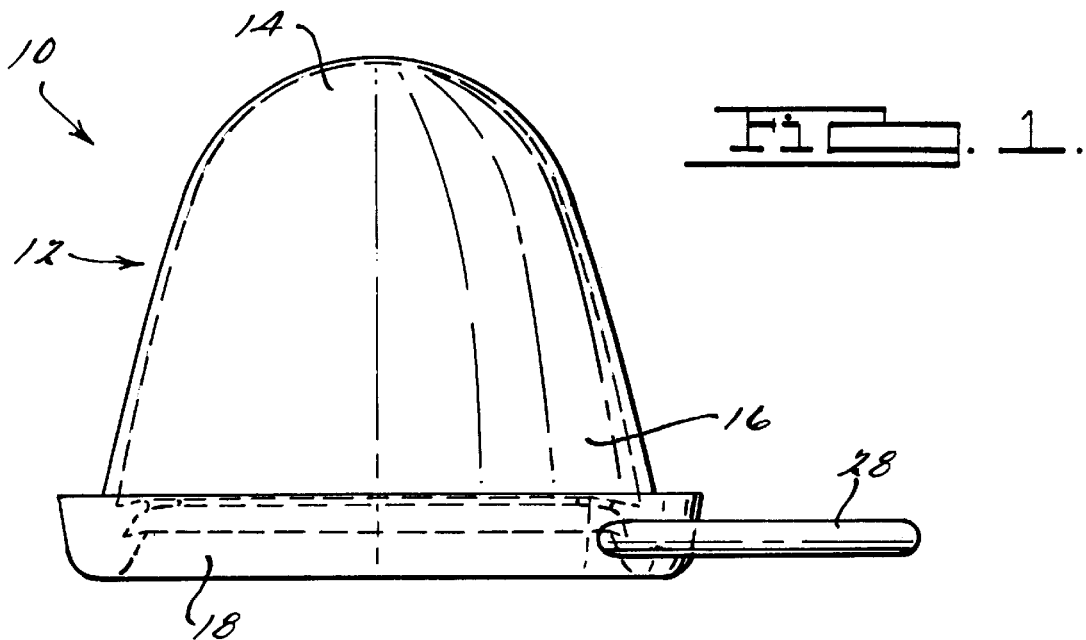
FIG. 1 is a side view of a preferred embodiment of a conception cap of the present invention.
Figure 2:
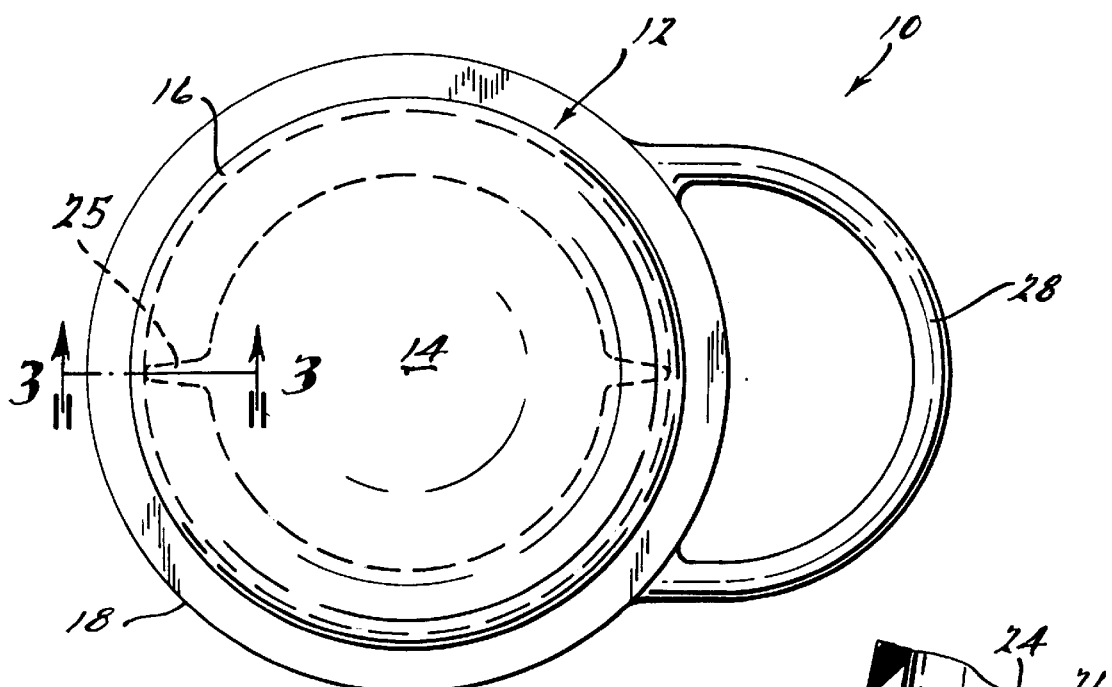
FIG. 2 is a top elevational view of the conception cap.
Figure 3:
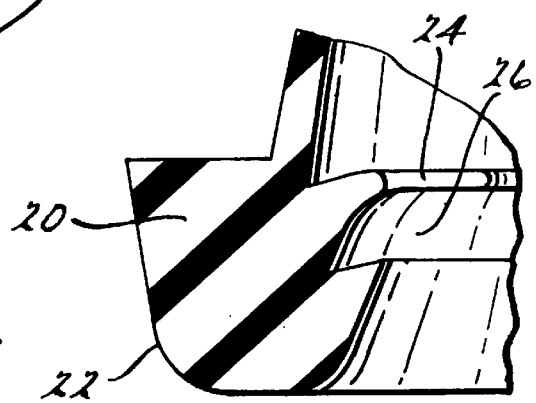
FIG. 3 is a sectional view, taken along line 3—3 in FIG. 2.

Referring to FIGS. 1–3, a preferred embodiment of a conception cap of the present invention is illustrated and indicated generally by the numeral 10. Generally speaking, conception cap 10 comprises a flexible, thin, form-assuming dome 12, a crown section 14, a base section 16, and an annular rim 18. Dome 12 is generally thimble-shaped, with base section 16 inwardly tapering toward crown section 14. The outer diameter of rim 18 is greater than that of base section 16 of dome 12.

Referring particularly to FIG. 3, annular rim 18 has an inner surface 20 and an outer surface 22. Thin, gripping finger 24 projects radially inwardly, as finger 24 is integrally-formed with inner surface 20. Finger 24 also defines an upper portion of a notched indentation 26 as viewed in FIG. 3. Annular rim 18 contains at least two gripping fingers 24 that are directly opposite or symmetrically opposed from each other along inner surface 20. However, it will be appreciated to one skilled in the art that more than two fingers could be employed.

Fingers 24 and notches 25 effectively grip and hold conception cap 10 over the cervix in order to concentrate the sperm at the Os of the cervix and to successfully effect fertilization. Gripping fingers 24 and notched indentation 25 essentially provide the effect of a chinese finger puzzle by gripping the side walls of the cervix and holding the cap when the circumference of the rim 18 is fitted around the cervix and slightly expands. Conception cap 10 is fixed in place by the use of gripping fingers 24 rather than merely by suction or surface viscosity. Thus, because of the rim construction, conception cap 10 is a size which is a suitable fit for a majority of women.

A handle 28 facilitates insertion and removal of conception cap 10, and is integrally-molded with annular rim 18. It is contemplated that dome 12, annular rim 18, gripping fingers 24, and handle 28 will preferably be made of a non-resilient flexible material, such as a silicone-based material. This material may or may not be impregnated with biologically active components. These components may be released therefrom in an amount effective to achieve its purpose during use.

Types of silicone-based materials suitable for use herein are known in the art and include high-consistency and low-consistency silicone-based elastomers prepared using a variety of well-known methods, e.g., platinum-cured systems, selected for compatibility with biological tissue and particular active ingredients being released by the conception cap. An example of a biologically active agent that could be released by the cap is one that would alter pH, or effect sperm activity. The elastomer can be loaded with the active agent in a manner appreciated by those skilled in the art that incorporates the agent in an excipient matrix with the elastomer, providing sustained release of the agent from the matrix.

Another preferred embodiment of the invention is the incorporation of conception cap 10, in all of its embodiments, in a conception kit to concentrate sperm and effect fertilization. The kit comprises the conception cap 10, an ovulation predictor, a condom and a pregnancy test. Ovulation predictors are well-known in the art and may be hormonal or temperature sensitive, such as a basel thermometer. Condoms are also well-known in the art, and for the purposes of the invention are preferably lambskin or polyurethane, but may be latex if the transfer of the sperm from the condom to the conception cap is fast enough to avoid damaging the sperm. Latex damages and kills sperm if it is in contact with the sperm for any significant amount of time. In addition, pregnancy tests are also well-known in the art and widely used.

The present invention also provides a method of achieving conception in a mammalian subject utilizing the conception kit. The method comprises the steps of:
a) determining the period of ovulation with an ovulation predictor,
b) providing viable sperm in a conception cap, and
c) inserting said conception cap into a vaginal cavity and positioning said cap over a cervix of a subject for a selected time period.

The method further comprises the steps of obtaining sperm by effecting ejaculation of the sperm into a condom, and carrying out a pregnancy test at the end of the procedure to determine whether fertilization occurred. Moreover, the silicone-based conception cap is a size which is a suitable fit for most women, as the thinness of the dome and rim construction allow for a flexible fit.

Although the description as set forth is in conjunction with human subjects, it will be further appreciated that the claimed compositions and methods may be readily adaptable for use with animal subjects having a cervix.

While it will be apparent that the preferred embodiments of the invention disclosed are well calculated to provide the advantages and features above stated, it will be appreciated that the invention is suspectable to modification, variation, and change without departing from the proper scope or fair meaning of the subjoined claims.

What is claimed is:

1. A conception cap positioned over a cervix to concentrate sperm and effect fertilization comprising:
   a thin, form-assuming, flexible dome having a hollow body and an interior and exterior surface, said dome comprising a crown section and base section,
   an annular rim integrally-molded with said base section having an inner and outer surface, and
   at least two thin, gripping fingers projecting radially inwardly, said fingers being integrally-formed with said inner surface of said rim, and at least two circumferentially spaced apart notches disposed between said fingers to permit said fingers to bend towards said crown section of said dome during insertion of said cap and to effectively grip and hold said cap over said cervix.

2. The conception cap of claim 1, wherein said cap is adapted to be used with isolated sperm within said body of said dome.

3. The conception cap of claim 1, wherein said cap further comprises a handle integrally-molded to said rim.

4. The conception cap of claim 1, wherein said cap is comprised of a silicone-based material.

5. The conception cap of claim 1, wherein said cap is comprised of a biologically active material.

6. The conception cap of claim 1, wherein a biologically active material is mixed with isolated sperm within said hollow body of said dome.

7. A conception kit to concentrate sperm and effect fertilization comprising (a) an ovulation predictor for determining the period of ovulation, (b) a conception cap comprising (1) a thin, form-assuming, flexible dome having a hollow body and an interior and exterior surface, said dome comprising a crown section and base section; (2) an annular rim integrally-molded with said base section having an inner and outer surface; and (3) at least two thin, gripping fingers projecting radially inwardly, said fingers being integrally-formed with said inner surface of said rim, and at least two circumferentially spaced apart notches disposed between said fingers to permit said fingers to bend towards said crown section of said dome during insertion of said cap and to effectively grip and hold said cap over said cervix; c) a condom for holding sperm until transferred to said conception cap, and (d) a pregnancy test for determining if fertilization occurred.

8. The conception kit of claim 7, wherein said ovulation predictor is hormonal.

9. The conception kit of claim 7, wherein said ovulation predictor is temperature sensitive.

10. The conception kit of claim 9, wherein said ovulation predictor is a basel thermometer.

11. The conception kit of claim 7, wherein said conception cap comprises a silicone-based material.

12. The conception kit of claim 7, wherein said condom is selected from the group consisting of lambskin, polyurethane, and latex.

13. A method of achieving conception in a mammalian subject having an ovulation period, comprising the steps of:
   a) determining the period of ovulation with an ovulation predictor, wherein said predictor is selected from the group consisting of a hormonal predictor and a temperature sensitive predictor;
   b) providing viable sperm in a conception cap; and
   c) inserting said conception cap into a vaginal cavity and positioning said cap over a cervix of a subject for a selected time period, wherein said cap comprises a silicone-based material.

14. The method of claim 13, wherein said subject is a human.

15. The method of claim 13, wherein said subject is an animal.

16. The method of claim 13, wherein said sperm is obtained by effecting ejaculation of said sperm into a condom, and further wherein said condom is selected from the group consisting of lambskin, polyurethane, and latex.

17. The method of claim 13, including a further step of carrying out a pregnancy test to determine whether fertilization occurred.

18. A conception cap positioned over a cervix to concentrate sperm and effect fertilization comprising:
   a thin, form-assuming, flexible dome having a hollow body and an interior and exterior surface, said dome comprising a crown section and base section;
   an annular rim integrally-molded with said base section having an inner and outer surface; and
   at least two thin, gripping fingers projecting radially inwardly, said fingers being integrally-formed with said inner surface of said rim, and at least two circumferentially spaced apart notches disposed between said fingers to permit said fingers to bend towards said crown section of said dome during insertion of said cap and to effectively grip and hold said cap over said cervix;
   wherein said cap is adapted to be used with isolated sperm within said body of said dome.

* * * * *

UNITED STATES PATENT AND TRADEMARK OFFICE
CERTIFICATE OF CORRECTION

PATENT NO. : 5,857,959
DATED : January 12, 1999
INVENTOR(S) : Michael LaVean et al It is certified that error appears in the above-identified patent and that said Letters Patent is hereby corrected as shown below:

Column 2, line 66, after "Fig. 2;" insert --and--.

Column 3, line 21, after "employed." insert --Fin 24 has at least two notches 25 to permit the fin to bend towards crown section 14 of dome 12 during insertion of the cap.--

Column 3, line 57, delete "Another" and insert --Referring now to Fig. 4, another--.

Column 3, line 61, after "predictor" insert --30--; after "condom" insert --32-- and after "test" insert --34, as shown in Fig. 4--.

Signed and Sealed this

Twenty-ninth Day of June, 1999

*Attest:*

Q. TODD DICKINSON

*Attesting Officer*  Acting Commissioner of Patents and Trademarks